United States Patent
Niederstadt et al.

(10) Patent No.: US 7,051,572 B2
(45) Date of Patent: May 30, 2006

(54) PROCESS FOR DETERMINING THE ODOR-INHIBITING PROPERTIES OF TEXTILE AUXILIARIES

(75) Inventors: Rule Niederstadt, Augsburg (DE); Rolf Moors, Bonstetten (DE); Alfred Weihrather, Schwabmünchen (DE); Jürgen Ellmann, Augsburg (DE); Felix A. Reifler, St. Gallen (CH); Axel Ritter, Waldstatt (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 17 days.

(21) Appl. No.: 10/498,608

(22) PCT Filed: Dec. 11, 2002

(86) PCT No.: PCT/EP02/14029

§ 371 (c)(1),
(2), (4) Date: Jun. 10, 2004

(87) PCT Pub. No.: WO03/052411

PCT Pub. Date: Jun. 26, 2003

(65) Prior Publication Data

US 2005/0081657 A1    Apr. 21, 2005

(30) Foreign Application Priority Data

Dec. 19, 2001  (DE) .............................. 101 62 300
Aug. 30, 2002  (DE) .............................. 102 39 972

(51) Int. Cl.
G01N 33/497    (2006.01)
(52) U.S. Cl. .................................... 73/23.34
(58) Field of Classification Search .............. 73/866, 73/23.34
See application file for complete search history.

(56) References Cited

U.S. PATENT DOCUMENTS

| | | | | |
|---|---|---|---|---|
| 3,815,405 A * | 6/1974 | Dravnieks | ................. | 73/23.34 |
| 4,770,027 A * | 9/1988 | Ehara et al. | ............... | 73/23.34 |
| 5,801,297 A | 9/1998 | Mifsud et al. | ............. | 73/23.34 |
| 6,050,129 A * | 4/2000 | Shefer | ...................... | 73/23.34 |
| 6,467,332 B1 * | 10/2002 | Bertschi et al. | ........... | 73/23.34 |
| 6,495,375 B1 * | 12/2002 | Ledig | ......................... | 436/181 |
| 6,511,852 B1 * | 1/2003 | Ledig | ......................... | 436/181 |

FOREIGN PATENT DOCUMENTS

DE    4035378        5/1992
DE    4035378 A1 *   5/1992

OTHER PUBLICATIONS

J. Payne et al., Textile Chemist and Colorist, vol. 28, No. 5, (1996), pp. 28-30.
B. J. Trask-Morrell et al., Textile Chemist and Colorist, vol. 27, No. 5, (1995), pp. 25-29.
Chem. Abstr. 117:113485 for DE 4035378 (1992).
English Language Abstract No. 637444 from the database Textiletech, published by the Institute of Textile Technology, for J. Wasko et al., Natural Fibers, 42, 63+, (1998).
English Language Abstract No. 607099 from the database Textiletech, published by the Institute of Textile Technology, for R. Weckmann, Co-Operation, Papers Presented at the World Conf., May 21-24 (1995).
English Language Abstract No. 589406 from the Database Textiletech, published by the Institute of Textile Technology, for H. Tsuiki et al., Sen-I Gakkaishi, 51, No. 5: 220+ (1995).
English Language Abstract 412220 from the Textiletech published by the Institute of Textile Technology, for B.A.K. Andrews, AATCC Book of Papers, Nat. Tech. Conf., 5-18, (Oct. 15-17, 1980).
English Language Abstract 610828 from the database Textiletech published by the Institute of Textile Technology, for J. Payne et al., INDA—Tec 96: Book of Papers, International Nonwovens Conf., (Sep. 11-13, 1996).
Chemical Abstr. 135:235558 for JP 2001242153 (2001).
English Language Abstract 644712 from the database Textiletech published by teh Institute of Textile Technology, for J. borgers, Nonwovens, Industrial Textiles, 47, No. 1: 35+ (2001).

* cited by examiner

*Primary Examiner*—Hezron Williams
*Assistant Examiner*—John Fitzgerald
(74) *Attorney, Agent, or Firm*—Kevin T. Mansfield

(57) ABSTRACT

Gaseous or volatile substances which are either themselves odor-active or components of odor-active mixtures of substances are applied to fabrics. The amount of these substances adsorbed by the textiles is then determined. It is then determined what amount of these substances is desorbed again by the textiles upon storage. Comparison of the results which are obtained on textiles which had been finished beforehand with textile auxiliaries with the results of non-finished textiles enables statements to be made regarding odor-inhibiting properties of textile auxiliaries.

6 Claims, No Drawings

PROCESS FOR DETERMINING THE ODOR-INHIBITING PROPERTIES OF TEXTILE AUXILIARIES

The invention relates to a process for determining the odor-inhibiting properties of textile auxiliaries.

BACKGROUND OF THE INVENTION

It is known that textiles adsorb gaseous or volatile substances from the surrounding atmosphere and can later desorb them again. When the desorbed substances have unpleasant odors, this property of the textiles may adversely affect their performance properties. Examples which may mentioned are drapes which smell of cigarette smoke or articles of clothing which emanate an odor of perspiration. Empirical findings state that the desorption properties of textiles can be affected by textile auxiliaries which are present on the surface of the textiles.

The prior art literature includes publications which have as the subject-matter odor properties or adsorption/desorption properties of textiles, e.g. abstract No. 637 444 from the database "Textiletech" (published by the Institute of Textile Technology) (=paper on "Natural Fibers, 42, 63+ (1998), J. Wasko et al., "New Quality Requirements and Test Methods for Cotton-Type Flax Fibers"), abstract No. 607 099 from the database "Textiletech" (published by the Institute of Textile Technology) (=paper on "Co-operation, Papers Presented at the World Conference, May 21–24, 1995", R. Weckmann, "Protection from Harmful Substances in Textiles; The Case of Oeko-tex Standard 100), also abstract No. 589 406 from the database "Textiletech" (published by the Institute of Textile Technology) (=paper on "Sen-i Gakkaishi, 51, No. 5, May 1995, H. Tsuiki et al., "Biomometic Oxidation of Thiol . . . "), abstract No. 412 220 from the database "Textiletech" (published by the Institute of Textile Technology) (=paper on "AATCC Book of Papers, Nat. Tech. Conf." 5–18 (Oct. 15–17, 1980, B. A. K. Andrews, "Extending the Relevance of the AATCC Sealed Jar Test for Formaldehyde Odor Determination"), abstract No. 610 828 from the database "Textiletech" (published by the Institute of Textile Technology) (=paper on INDA-TEC 96: Book of Papers: International Nonwovens Conference, Sep. 11–13, 1996, J. D. Payne et al., "A New Use of Polymeric Biguanide as an Antimicrobial Agent on Cellulosics")

and chemical abstract No. 135: 235 558 CA (=paper on "JPN Kokai Tokkyo Koho" S. Tokunaga et al., "Method and Device fo Measurement of Capacity of Deodoring Material").

D. Eisele describes in Vliesstoffe, Technische Textilien 1/2001 "Untersuchungen zur Ad-/Ab-Desorption eines Riechkörpers von Textilfasern" [Investigations regarding the Adsorption/Desorption of an Odorant by Textile Fibers].

BRIEF SUMMARY OF THE INVENTION

The object of the present invention was to develop a process which permits the determination of the odor-inhibiting properties of textile auxiliaries toward gaseous or volatile substances.

The object was achieved by a process for determining the odor-inhibiting properties of textile auxiliaries, where the following process steps a) to e) are carried out with a fabric to which the textile auxiliary to be investigated has been applied beforehand, and additionally with a fabric of the same provenance to which this textile auxiliary has not been applied:

a) application of a gaseous or volatile substance (substance A) to a fabric.

b) either b1) extraction of a sample of the resulting fabric with a solvent in which substance A is readily soluble or b2) heating a sample of the fabric obtained after carrying out step a) in a closed apparatus under conditions under which essentially complete desorption of substance A into the gas phase takes place, but no chemical decomposition of substance A c) determination of the amount of substance A extracted when carrying out step b1), or determination of the amount of substance A present in the gas phase after carrying out step b2), d) storage of another sample of the fabric obtained after step a) at room temperature in a closed apparatus.

e) determination of the amount of substance A present after step d) in the gas phase in the closed apparatus, where substance A is either itself odor-active or a component of an odor-active mixture of substances, where steps d) and e) can be carried out from the point of view of time before or after steps b) and c).

This process can be used to formulate statements as to whether a textile auxiliary which is present on a fabric has odor-inhibiting properties. These properties are to be assumed if a textile finished with the textile auxiliary desorbs odor-active gaseous or volatile substances to a lesser degree than a textile of the same provenance which has been treated under identical conditions except that the textile auxiliary has not been applied to the textile.

The principle of the process according to the invention consists in applying a gaseous or volatile substance (substance A) under controlled conditions to a fabric, determining the amount of this substance adsorbed by the fabric and determining the amount of this substance which is desorbed by the fabric under controlled conditions. By comparing the results which are obtained with a non-finished textile material and a textile material finished using a textile auxiliary it is possible to formulate statements regarding odor-inhibiting (=desorbing) properties of the textile auxiliary. These statements can be used for selecting textile auxiliaries for the finishing of textiles.

The fabrics with which the process according to the invention can be carried out may be wovens, knits or nonwovens. Preference is given to using wovens. Suitable for this purpose are, for example, wovens as are used for the preparation of articles of clothing or of household textiles such as furniture covers or drapes. Said finished articles are subjected in a particular manner to the adsorption of substances with an unpleasant smell, such as tobacco smoke, perspiration, feces, kitchen odors or substances with a pleasant odor, such as perfumes. The fabrics can consist of any desired fibers or fiber mixtures. Suitable fibers are wool, synthetics such as polyamide or acrylic fibers. Particularly suitable fabrics for carrying out the process according to the invention are those which consist of 100% of cellulose fibers, e.g. cotton, or polyester fibers, e.g. polyethylene terephthalate, or a mixture of cellulose and polyester fibers.

DETAILED DESCRIPTION OF THE INVENTION

The first step of the process according to the invention consists in applying a substance (substance A) to a fabric. This substance is solid, liquid or gaseous under atmospheric pressure and at room temperature and it is volatile, and it is either itself odor-active or it is a component of a mixture of substances which is odor-active. Odor-active substances are understood as meaning substances or mixtures of substances which can be perceived by the human sense of smell. In order that this perception can take place, the substances must either be gaseous or volatile. "Volatile" means that they must have a minimum value for the vapor pressure at room temperature and atmospheric pressure. This minimum value is different from substance to substance and is such that the human sense of smell can perceive the substance in the environment of a sample of the substance which is in contact with the surrounding atmosphere.

It is not absolutely necessary for substance A itself to be odor-active, although this is preferred. It may also be a non-odor-active component of an odor-active mixture of two or more substances, e.g. when the amount of a non-odor-active substance A which is present in an odor-active mixture of substances is analytically easier to determine in step c) and/or e) of the process according to the invention (e.g. by gas chromatography) than the amount of the entire substance mixture. However, in this case the non-odor-active substance A should be present in the odor-active substance mixture in not too small an amount in order that the inaccuracy which results when extrapolating the ascertained amount of substance A to the whole mixture does not become too great. Thus, in this case, it is advisable for the non-odor-active substance A to be present in the odor-active overall mixture in an amount of at least about 30% by weight. However, the substance A which is used in the process according to the invention is preferably itself odor-active. In the text below, therefore, the substance A is referred to as odor-active. However, this does not exclude the above variant, according to which substance A is itself non-odor-active, but rather a component of an odor-active mixture.

The gaseous or volatile, odor-active substance (substance A) can consist of a uniform chemical compound or of a mixture of two or more compounds. Preferably, for the process according to the invention, the odor-active gaseous or volatile substances used are those substances or mixtures of substances with which textiles come into contact in practice. Such substances can have a pleasant odor, such as perfumes and components thereof, or an unpleasant odor, such as tobacco smoke or human perspiration or feces or individual components thereof. Preference is given to carrying out the process according to the invention with the substances mentioned here.

The process according to the invention is particularly suitable for ascertaining the odor-inhibiting properties of textile auxiliaries toward nicotine or toward a branched or unbranched aliphatic, saturated or monounsaturated monocarboxylic acid having 4 to 12 carbon atoms or toward a mixture of such substances. The monocarboxylic acids mentioned here are typical ingredients of human perspiration.

In addition, the process according to the invention can also be carried out with other odor-active substances with which textiles may come into contact in practice. Examples thereof are substances or substance mixtures which arise in kitchen odors, such as odors from foods or oil heated during frying or components of feces. Certain amines with which textiles come into contact can also be used as substances A in process step a).

In the first step (step a)) of the process according to the invention (which is carried out both on fabric to which the textile auxiliary to be investigated has been applied beforehand, and also to a fabric of the same provenance to which the textile auxiliary has not been applied) the substance A to be investigated is applied to a fabric. This application may be carried out by a number of methods. The preferred method consists in storing the fabric, e.g. a cotton fabric, in a closed apparatus in an atmosphere which contains the substance A. The gas phase can here be saturated with this substance. Storage preferably takes place at room temperature and for a sufficiently long residence time so that the textile can adsorb sufficient substance A to achieve an equilibrium state.

Other, but less preferred, methods of application consist in spraying the substance A or a solution of the substance in a low-boiling solvent, or impregnating the textile with the substance or a solution of the substance.

One variant of the process according to the invention which is particularly suitable and geared toward practice consists in determining the odor-inhibiting or adsorbing and desorbing properties of the two fabrics toward nicotine and is characterized in that, in step a), nicotine is used as substance A and is applied to the fabrics by storing the fabrics in a closed apparatus in an atmosphere containing nicotine.

A second and third step (step b) and c)) of the process according to the invention determines in each case on one sample of the fabric obtained in step a) what amount of the odor-active substance A has been adsorbed by the textile. This determination should take place as soon as possible after step a), e.g. after a period of not more than a few minutes in order to prevent relevant amounts of substance A being desorbed from the textile prior to step b) being carried out.

If steps b) and c) are not to be carried out from the point of view of time as the second and third step of the process according to the invention, but only later as step d) and e) (which, as mentioned below, is possible, but not preferred), then, after step a) has been carried out, the fabric containing substance A must be stored under conditions such that no or at most insignificant amounts of substance A are removed by evaporation from the fabric prior to step b) being carried out.

In step b) of the process according to the invention, the amount of substance A adsorbed by the textile in step a) is removed again from the textile essentially completely. In step c), the amount of substance A which has been removed from the textile in step b) is determined analytically.

Step b) can be carried out in accordance with two different methods, namely as step b1) or as step b2). These two alternatives are described below.

In step b1), the sample of the fabric is in each case extracted with a solvent, where necessary at elevated temperature. In many cases, acetone is a particularly suitable solvent. The extraction should be carried out such that essentially the entire amount of substance A is extracted, such that, after step b1), at most trace amounts of substance A remain on the textile. Details for carrying out step b1) are described below.

In step b2), the sample of the fabric is in each case heated in a closed apparatus under temperature and residence-time conditions such that essentially complete desorption of substance A into the gas phase takes place, but no chemical decomposition of substance A. In this connection, essentially complete desorption means that, after step b2), at most trace amounts of substance A remain on the textile. Details for carrying out step b2) are described below.

In process step c), the amount of substance A removed from the textile in step b1) or b2) is analytically determined. This determination is preferably carried out by means of gas chromatography. Even at this point it may be mentioned that the determination according to process step e) described below also preferably takes place by means of gas chromatography. However, both for step c) and also for step e), it is also possible to apply analytical methods other than gas chromatography. Such methods are known to the analytical chemist. Further details for carrying out step c) and e) by means of gas chromatography are described below.

Steps b) and c) can be carried out from the point of view of time before or after steps d) and e) described below. However, preference is given to carrying out steps b) and c) in the shortest possible time after step a), and only then steps d) and e).

Step d) in the process according to the invention consists in bringing about in each case on another sample of the fabrics obtained in step a) a desorption of substance A at room temperature. For this, a sample of the textile which has not been subjected to step b) is used in each case. The desired desorption is effected by storing the sample at room temperature in a closed apparatus. The storage time is governed here according to the individual case; the storage should be carried out until an equilibrium distribution of substance A between gas phase and fabric has been established.

In process step e), finally, the amount of substance A which has passed from the textile into the gas phase while carrying out step d) is determined. This analytical determination is preferably carried out by means of gas chromatography. Details regarding this are described below.

By comparing the results on a textile material which had been finished prior to carrying out the process with a textile auxiliary (TA) with the results which are obtained on a non-TA-finished textile, it is possible to formulate statements as to whether the TA used has odor-inhibiting properties. Particularly when the amount of substance A desorbed during step d) is markedly lower for the TA-finished textile material than in the case of the non-finished textile material, it is possible to speak of an odor-inhibiting effect of the TA. In order to obtain meaningful results, the non-finished textile material must be of the same provenance as the finished material. This means that the two samples consist of the same material and must have been subjected to the same process steps during the manufacture, the single difference being that a TA has been applied to one of the samples and not to the other.

In this connection, textile auxiliaries (TA) are understood as meaning products which are applied to fabrics during the finishing process in a last step prior to manufacturing. Such TA are known to the person skilled in the art. These are the products usually used for textile finishing. These include fabric softeners, such as waxes, fatty acid derivatives and polyorganosiloxanes, where, in particular, amino-functional polyorganosiloxanes, in particular, are suitable, and also water-repellent agents, such as polysiloxanes, or oil-repellent agents, such as polymers with perfluoroalkyl groups, cellulose crosslinkers, such as ethyleneureas, which are optionally methylolated and optionally etherified, and optionally corresponding dihydroxyethyleneureas, where these ureas may optionally be used in combination with melamine derivatives, and flame-retardant products, such as N-methylolphosphonopropionamides or amine salts of alkylphosphonic acids. The application of such TA to the fabrics can be carried out by known methods, e.g. by padding and subsequent drying and optional curing at temperatures above 100° C. In order to formulate a statement regarding the odor-inhibiting properties of a TA by the process according to the invention, the textile material not finished with TA should be pretreated in an identical manner prior to carrying out the process, but without applying a TA, i.e. thus, e.g. also to a padding under the same conditions as in the case of the sample finished with TA, where the liquor comprises only water, and subsequent drying and optional curing.

The process according to the invention can be used inter alia also for determining the odor-inhibiting properties of cyclodextrins, namely by using one or more cyclodextrins as textile auxiliaries (TA) or a composition which comprises one or more cyclodextrins. It is known from the prior art that cyclodextrins can adsorb odor-active substances.

Cyclodextrins are understood here as meaning cyclically closed oligosaccharides which consist of 6, 7 or 8 α-1,4-glycosidically linked D-glucopyranose units, corresponding to the definition in H. R. Christen et al. "*Organische Chemie. Von den Gnundlagen zur Forschung*", volume 11, page 549, 1st edition 1990, Otto-Salle-Verlag, Frankfurt/M. In this connection, α-cyclodextrin, β-cyclodextrin and γ-cyclodextrin mean the compounds with 6, 7 and 8 units, respectively.

Cyclodextrins form during the degradation of starch by bacteria. Preference is given to using β-cyclodextrin.

Cyclodextrins are standard commercial products, e.g. obtainable from Wacker Chemie, Germany.

The text below describes preferred methods for carrying out steps a) to e) of the process according to the invention, each of which can be carried out on fabric samples finished with TA and not finished with TA.

Step a):

To carry out step a) of the process according to the invention, the following procedure may be followed:

A fabric, e.g. a fabric with the measurements 5×5 cm or 5×10 cm, is preconditioned over several hours at room temperature and a relative atmospheric humidity in the range 20–45%. The fabric sample is then transferred to a hermetically sealable glass vessel. Then, by applying a pressure below atmospheric pressure, the majority of the air present in the gas phase is removed. If the odor-active substance A to be investigated is gaseous, substance A is then introduced directly into the gas phase. Where substance A is cigarette smoke, this can be generated by means of a commercial smoking machine. If, by contrast, substance A is liquid, e.g. one or more carboxylic acids which arise in human perspiration, then the liquid substance A can be injected into the hermetically sealable vessel. In this case, the fabric sample should be covered with a gas-permeable, liquid-impermeable barrier layer, e.g. with a membrane, in order to prevent liquid passing directly onto the fabric. Alternatively to this, it is also possible to place a defined amount of sand, preferably quartz sand with a low surface area, into the vessel, and to spray the liquid substance A onto the sand and optionally to distribute it optimally by shaking. In each case, the amount of substance A added to the hermetically sealable vessel should be such that the fabric can adsorb the amount of substance A corresponding to saturation. Following the addition of substance A, the vessel is hermetically sealed and left to stand at room temperature or at elevated temperature, e.g. up to 80° C. until the maximum possible amount of substance A is adsorbed by the fabric. For this, experience shows that a storage period of from 15 minutes to 20 hours suffices. However, in individual cases, significantly longer storage times may also be suitable, e.g. 20 to 100 hours.

Following the storage, the fabric sample is either added to another hermetically sealable vessel in which the gas phase consists of ambient air, and then step b2) of the process according to the invention is carried out.

Alternatively, the fabric sample is subjected directly to extraction according to step b1) after carrying out step a) and storage.

Step b1):

In step b1), the amount of substance A which has been taken up by the fabric while carrying out step a) is extracted. In many cases, acetone has proven to be a suitable solvent for carrying out step b1). The extraction is carried out, optionally at elevated temperature, until virtually the entire amount of the substance A adsorbed in step a) has been extracted.

Step b2):

In step b2), the amount of substance A which has been taken up by the fabric while carrying out step a) is desorbed. Preferably, step b2) is carried out by hermetically sealing the vessel into which the fabric sample was introduced after step a) and then heating it. The heating time and temperature are such that the entire amount of substance A is essentially desorbed from the textile and passes into the gas phase. The temperature here must be chosen so that no chemical decomposition of substance A arises. In the case of nicotine as substance A, the temperature is about 160° C. and the heating time is about 20 to 30 minutes.

Step c):

In step c), the amount of substance A which has been removed (desorbed or extracted) from the textile in step b) is determined. Preference is given to using gas chromatography (GC) as the determination method, e.g. directly on the extract or else following removal of the solvent if a step b1) had been carried out previously; the second variant is naturally only possible if the solvent can be removed without simultaneously removing noteworthy amounts of the substance A from the extract. For the detection, flame ionization detection (FID) or mass spectrometry (MS) are suitable. For this purpose, the extract which was obtained after carrying out step b1) is passed to a gas chromatograph, optionally following prior removal of the solvent.

If a step b2) had previously been carried out, the gas phase which is located in the tightly sealed vessel after carrying out step b2) can be removed by suction and passed directly to a gas chromatograph.

The method described for carrying out step b2) and c) is referred to as the "headspace" method.

The process steps d) and e) described below are carried out on in each case a TA-finished and a non-finished fabric sample, which have been obtained according to step a), but not been subjected to steps b) and c).

Step 1d):

This step is carried out on fabric samples which have been subjected to step a), but not to steps b) and c).

In step d), a desorption of substance A is carried out at room temperature. This step consists in desorbing not the total amount of substance A from the textile, but only enough to achieve an equilibrium distribution of substance A between fabric and gas phase. This corresponds to practical conditions during use of textiles.

To carry out step d), the fabric is stored at room temperature until the mentioned equilibrium has been established. The gas phase here is ambient air. The storage time is between 30 and 90 minutes and must of course be exactly as long for the TA-finished sample as for the non-finished sample.

The storage takes place in a hermetically sealed vessel. Following storage (step d)), step e) of the process according to the invention is carried out.

Step e):

In this step, the amount of substance A which has been released from the fabric into the gas phase in step d) is determined. As in step c), this determination is preferably carried out by means of gas chromatography, coupled with FID or MS.

Preferably, steps d) and e) are carried out by means of the SPME (solid phase microextraction) or via the known SPDE (solid phase dynamic extraction) method. The SPME method involves, after step d), inserting a hollow needle into the hermetically sealed vessel, in the cavity of which needle there is a cylindrical insert which can be moved up and down by means of a piston. The cylinder consists of a fiber or of a film made of a polymer which is coated. This fiber can, for example, be in the form of a quartz fiber. The coating consists of a material which is readily adsorbing toward substance A, e.g. a modified polyorganosiloxane or an acrylic polymer, or a copolymer of polydimethylsiloxane and divinylbenzene.

While carrying out step d), the coated cylinder is inserted into the gas phase above the fabric sample and takes up the amount of substance A desorbed by the fabric sample. The coated fiber or the coated film on which the amount of substance A desorbed from the fabric is located can be passed directly to the GC. Alternatively to this, the substance A can be detached from the cylinder beforehand using a solvent.

The SPDE method consists in, after step d), inserting a hollow needle of a hermetic injection syringe into the hermetically sealed vessel. The hollow needle is coated on the inside with a fiber or a film of a polymer. The fiber may, for example, be in the form of a quartz fiber. The coating consists of a material which is readily adsorbing toward substance A, e.g. a modified polyorganosiloxane or an acrylic polymer, or a copolymer of polydimethylsiloxane and divinylbenzene. To enrich the fiber/film of the polymer with substance A, the sample is repeatedly flushed through the hollow needle.

While carrying out step d) in accordance with the SPDE method, the hollow needle is inserted into the gas phase above the fabric sample and takes up the amount of substance A desorbed from the fabric sample. The coated fiber or the coated film on which the amount of substance A desorb from the fabric is located can be passed directly to the gas chromatography (GC). Alternatively to this, the substance A can be detached from the coating beforehand using a solvent and then passed to the GC.

The invention is illustrated below by working examples.

EXAMPLE 1

An undyed fabric made of 100% cotton was divided into 2 samples. One sample was finished with a textile auxiliary, the other was not. The two samples were then subjected to the process according to the invention. The textile auxiliary (TA) comprised the following constituents:

a) behenic acid b) β-cyclodextrin c) quaternary ammonium salt (=emulsifier)

d) dimethyloldihydroxyethyleneurea (methanol-etherified)

e) $MgCl_2 \times 6H_2O$ (=catalyst)

Finishing Conditions:

The fabric sample was finished using a padding process (3 g of a), 2 g of b), 5.2 g of c), 21 g of d), 12 g of e) per l of liquor, liquor pick-up by the fabric after squeezing: 80% by weight, based on nonfinished fabric); drying: 110° C./10 minutes, curing: 150° C./5 minutes.

Step a)

In each case one sample (5×10 cm) of the TA-finished and the non-finished preconditioned fabric sample were each introduced separately into a hermetically sealable glass bottle (volume 20 ml) which was provided with an injection device consisting of a storage vessel and an injection needle. The storage vessel was charged with a mixture comprising 34 parts by weight of methyl 2-hexen-1-oate 180 parts by weight of valeric acid 185 parts by weight of butyric acid These acids are typical ingredients or degradation products of human perspiration. A gas-permeable, liquid-impermeable membrane was located above the fabric sample in the bottle. 0.1 µl of said carboxylic acid mixture was injected into the bottle. The bottle was left to stand for 70 hours at room temperature in order to permit adsorption of the acid mixture by the fabric.

Steps b1) and c) (Extraction and Analysis):

After carrying out step a), the two fabric samples were each introduced separately into a bottle, as had been used for step a). Then, at room temperature, the amount of substance A which was taken up by the fabric while carrying out step a) was extracted. The extraction solvent chosen was acetone. The extraction was carried out until virtually the entire amount of the substance A adsorbed in step a) had been extracted. The extract was then introduced directly into a gas chromatograph (Hewlett-Packard HP 5890, column: HP 5, with the data 30 m×0.32 mm×0.52 µm film, injection temperature 250° C., detector: flame ionization detection at 290° C.).

Step d):

In each case one sample of non-TA-finished and TA-finished fabric which had been subjected to step a), but not to steps b1) and c) were subjected separately from one another to the following step d):

The fabric samples were each introduced into a hermetically sealable bottle of the type described above. The bottles were then closed and stored for 30 minutes at room temperature in order to effect desorption of the applied acid mixture from the textile into the gas phase. Onto the bottle was placed a device which had a cylindrical cavity in which there was located a movable cylindrical rod made of quartz fiber. This quartz fiber rod was coated with a modified polydimethylsiloxane which had good adsorption properties toward gaseous substances. After storage for 30 minutes, the movable rod made of coated quartz fiber was introduced into the gas space of the bottle and left in the gas space for 30 minutes.

Step e):

Here, the amount of acid mixture adsorbed by the quartz rod was determined analytically. For this purpose, the rod was introduced directly into the injector of the gas chromatograph described above, injection temperature: 280° C., detection: flame ionization detector.

EXAMPLE 2

The same experiments as in Example 1 were carried out on fabric samples made of 100% polyester (polyethylene terephthalate).

EXAMPLES 3 AND 4

Examples 1 and 2 were carried out with the following changes (Example 3 relates to the investigations on cotton fabric, Example 4 those on polyester fabric):

Instead of the mixture of carboxylic acids, cigarette smoke was used as the odor-active substance. This smoke was generated using a commercial so-called smoking machine and introduced directly in each case in step a) to a desiccator where the fabric sample was located. After carrying out step a), the fabric samples were in each case introduced into a hermetically sealable bottle of the type mentioned above. Then, steps b1) and c) or d) and e) were carried out, as stated in Example 1. In the gas chromatographic analyses, the amount of nicotine in each case was determined.

EXAMPLE 5

Example 1 was repeated with the following changes:

In step a), 10 µl of a mixture of 3-methyl-2-hexenoic acid (cis-trans mixture) ("perspiration component")

benzyl acetate (perfume component)

nicotine 3-methylindole (constituent of feces)

was injected into the storage vessel in the manner described above. The bottle was left to stand at room temperature for 70 hours in order to permit adsorption of the mixture by the fabric.

In the analytical determinations by means of gas chromatography, each of the 4 aforementioned constituents was analyzed separately.

EXAMPLES 1a TO 4a)

Examples 1 to 4 were repeated with the following deviations.

For process step a), a fabric sample with the dimensions 2×2 cm was used. The storage time for process step a) following injection of the carboxylic acid mixture was 15 minutes (instead of 70 hours as for Examples 1 to 4).

Steps b) and c) were carried out as follows:

After carrying out step a), the two fabric samples were in each case introduced separately into a bottle, as had also been used for step a). The atmosphere in this bottle consisted of ambient air. The bottle was hermetically sealed and heated at 160° C. for 20 minutes. The gas phase was then introduced directly to a gas chromatograph (Hewlett-Packard HP 5890, column: HP 5, with the data 30 m×0.32 mm×0.52 µm film, injection temperature 250° C., detector: flame ionization detection at 290° C.).

Thus, step b) was variant b2) (thermal desorption instead of extraction as in Examples 1 to 4).

Results

The results are given in Table 1.

TABLE 1

|  | Q total | Q desorption |
|---|---|---|
| Example 1 and Example 1a ("perspiration acids", cotton) | 4 | 0.7 |
| Example 2 and Example 2a ("perspiration acids", polyester) | 3 | 0.8 |
| Example 3 and Example 3a (cigarette smoke, cotton) | 4 | 0.7 |
| Example 4 and Example 4a (cigarette smoke, polyester) | 3 | 0.8 |
| Example 5 (mixture of 3-methyl-2-hexenoic acid, nicotine, benzyl acetate and 3-methylindole, cotton) | 2 | 0.8 |

The following meanings apply here:

$Q$ total=the quotient $x/y$ x=total amount of odor-active substance which was adsorbed by the TA-finished fabric (determined according to steps b1) or b2) and c))

y=total amount of odor-active substance which was adsorbed by the non-TA-finished fabric (determined according to steps b1) or b2) and c))

$Q$ desorption=the quotient $u/v$ u=the amount desorbed from the TA-finished fabric at room temperature (according to steps d) and e))

v=the amount desorbed from the non-TA-finished fabric at room temperature (according to steps d) and e))

As Table 1 shows, the same results were obtained for Examples 1 to 4 as for Examples 1a to 4a. The results found were thus independent of whether step b) was carried out according to variant b1) (extraction) or variant b2) (desorption).

The fact that Q desorption is less than 1 in all cases means that the TA used has odor-inhibiting properties with regard to the odor-active substances used ("perspiration acids", nicotine, perfume or feces component) both in the case of cotton fabric and also in the case of polyester fabric.

In further experiments, it was found that the results obtained during the measurements and thus the extent of the odor-inhibiting properties of textile auxiliaries can be influenced by the moisture content of the fabric samples.

What is claimed is:

1. A process for determining the odor-inhibiting properties of textile auxiliaries, where the following process steps a) to e) are carried out with a fabric to which the textile auxiliary to be investigated has been applied beforehand, and additionally with a fabric of the same provenance to which this textile auxiliary has not been applied:
    a) application of a gaseous or volatile substance (substance A) to a fabric,
    b) either
    b1) extraction of a sample of the resulting fabric with a solvent in which substance A is readily soluble or
    b2) heating a sample of the fabric obtained after carrying out step a) in a closed apparatus under conditions under which essentially complete desorption of substance A into the gas phase takes place, but no chemical decomposition of substance A,
    c) determination of the amount of substance A extracted when carrying out step b1), or determination of the amount of substance A present in the gas phase after carrying out step b2),
    d) storage of another sample of the fabric obtained after step a) at room temperature in a closed apparatus,
    e) determination of the amount of substance A present after step d) in the gas phase in the closed apparatus, where substance A is either itself odor-active or a component of an odor-active mixture of substances, where steps d) and e) can be carried out from the point of view of time before or after steps b) and c).

2. A process as claimed in claim 1, wherein substance A is tobacco smoke, human perspiration and/or a perfume and/or a component present in tobacco smoke, human perspiration or perfume.

3. A process as claimed in claim 1, wherein substance A is nicotine or an unbranched aliphatic, saturated or monounsaturated monocarboxylic acid having 4 to 12 carbon atoms.

4. A process as claimed in claim 1, wherein, in step a), nicotine is used as substance A and is applied to the fabric by storing the fabric in a closed apparatus in an atmosphere containing nicotine.

5. A process as claimed in claim 1, wherein the fabric consists of 100% by weight of cellulose fibers or polyester fibers or a mixture of these types of fiber.

6. A process as claimed in claim 1, wherein the determination according to step c) and/or e) is carried out by means of gas chromatography.

* * * * *